United States Patent
Irion et al.

(10) Patent No.: US 9,028,399 B2
(45) Date of Patent: May 12, 2015

(54) INTRACORPOREAL VIDEOCAPSULE WITH SWIVELING IMAGE PICKUP

(75) Inventors: Klaus M. Irion, Emmingen-Liptingen (DE); Fritz Hensler, Neuhausen (DE); Christine Harendt, Muehlacker (DE); Heinz-Gerhard Graf, Magstadt (DE); Robert Puers, Blanden (BE); David Turgis, Leuven (BE); Bert Lenaerts, Kortessem (BE); Alberto Arena, Cascina (IT); Arianna Menciassi, Pontedera (IT); Vassilis Kodogiannis, Crete (GR)

(73) Assignee: Karl Storz GmbH & Co. KG (DE)

( * ) Notice: Subject to any disclaimer, the term of this patent is extended or adjusted under 35 U.S.C. 154(b) by 1567 days.

(21) Appl. No.: 11/867,324

(22) Filed: Oct. 4, 2007

(65) Prior Publication Data
US 2008/0081947 A1 Apr. 3, 2008

Related U.S. Application Data

(63) Continuation of application No. PCT/EP2006/003054, filed on Apr. 4, 2006.

(30) Foreign Application Priority Data

Apr. 4, 2005 (DE) .......................... 10 2005 015 522

(51) Int. Cl.
*A61B 1/06* (2006.01)
*A61B 1/04* (2006.01)
*A61B 1/00* (2006.01)

(52) U.S. Cl.
CPC .............. *A61B 1/041* (2013.01); *A61B 1/00016* (2013.01); *A61B 1/00029* (2013.01); *A61B 1/00032* (2013.01); *A61B 1/00183* (2013.01); *A61B 2560/0219* (2013.01)

(58) Field of Classification Search
CPC ............. A61B 1/0008; A61B 1/00096; A61B 1/00172; A61B 1/00183; A61B 1/041; A61B 1/05; A61B 1/00016; A61B 1/00156; A61B 1/0032; A61B 1/00029; A61B 1/051; A61B 1/0684
USPC ................. 600/103, 109, 142, 173, 147, 175; 348/211.99
See application file for complete search history.

(56) References Cited

U.S. PATENT DOCUMENTS

| 5,604,531 A | 2/1997 | Iddan et al. |
| 5,617,762 A | 4/1997 | Kirsch |

(Continued)

FOREIGN PATENT DOCUMENTS

| DE | 42 09 536 | 9/1993 |
| DE | 199 55 229 | 8/2001 |

(Continued)

OTHER PUBLICATIONS

Product pamphlet for IMS Chips HDRC Imager (Sep. 2002), retrieved from http://www.ims-chips.de/content/pdftext/HDRC_Imager_Camera_Feature3.pdf.*

(Continued)

*Primary Examiner* — Anhtuan T Nguyen
*Assistant Examiner* — William Chou
(74) *Attorney, Agent, or Firm* — St. Onge Steward Johnston & Reens LLC

(57) ABSTRACT

The invention relates to an intracorporeal probe (10), for example preferably for examining hollow organs or natural or artificially created body cavities in the human or animal body, the probe (10) being designed in the form of a capsule that can be introduced into the body without external connecting elements, comprising an elongate housing (16) and an image pickup unit (26) inside the housing (16) that is designed for optically recording a region (pickup region) outside the probe (10). The image pickup unit (26) is held in a fashion capable of moving inside the housing (16) in order to vary the pickup region by means of such a movement (FIG. 1).

21 Claims, 5 Drawing Sheets

(56) References Cited

U.S. PATENT DOCUMENTS

| | | | |
|---|---|---|---|
| 6,371,909 B1* | 4/2002 | Hoeg et al. | 600/173 |
| 6,464,631 B1 | 10/2002 | Girke et al. | |
| 2001/0038258 A1* | 11/2001 | Fischer et al. | 310/328 |
| 2002/0103417 A1* | 8/2002 | Gazdzinski | 600/109 |
| 2002/0128538 A1 | 9/2002 | Thompson | |
| 2002/0165592 A1 | 11/2002 | Glukhovsky et al. | |
| 2002/0176006 A1* | 11/2002 | Miura | 348/211.99 |
| 2003/0130562 A1 | 7/2003 | Barbato et al. | |
| 2003/0195415 A1 | 10/2003 | Iddan | |
| 2004/0027459 A1* | 2/2004 | Segawa et al. | 348/207.99 |
| 2004/0249245 A1 | 12/2004 | Irion | |
| 2005/0043583 A1 | 2/2005 | Killmann et al. | |
| 2005/0119577 A1* | 6/2005 | Taniguchi | 600/459 |
| 2005/0143644 A1* | 6/2005 | Gilad et al. | 600/407 |
| 2006/0167339 A1* | 7/2006 | Gilad et al. | 600/101 |
| 2006/0224040 A1* | 10/2006 | Khait et al. | 600/102 |
| 2010/0324381 A1* | 12/2010 | Glukhovsky et al. | 600/302 |

FOREIGN PATENT DOCUMENTS

| | | |
|---|---|---|
| DE | 101 46 197 | 4/2003 |
| DE | 103 23 216 | 12/2004 |
| EP | 0 667 115 | 8/1995 |
| JP | 07327916 | 12/1995 |

OTHER PUBLICATIONS

International Search Report, Jul. 10, 2006, 4 pages.
Written Opinion, Jul. 17, 2006, 8 pages.
European Examination Report; Application No. EP 06 724 010.1; Issued: May 9, 2011; 5 pages.

* cited by examiner

INTRACORPOREAL VIDEOCAPSULE WITH SWIVELING IMAGE PICKUP

CROSS REFERENCES TO RELATED APPLICATIONS

This application is a continuation of international patent application WO 2006/105932 A1 (PCT/EP2006/003054), filed on Apr. 4, 2006, designating the U.S., which international patent application has been published in English language and claims priority from German patent application DE 10 2005 015 522, filed on Apr. 4, 2005. The entire contents of these priority applications are incorporated herein by reference.

BACKGROUND OF THE INVENTION

The present invention relates to an intracorporeal probe, for example preferably for examining hollow organs or natural or artificially created body cavities in the human or animal body, the probe being designed in the form of a capsule that can be introduced into the body without external connecting elements, comprising a housing and an image pickup unit inside the housing that is designed for optically recording, for example imaging, a region (termed pickup region below) outside the probe.

An intracorporeal probe of the aforesaid type is known in general, for example from DE 101 46 197. EP-A-0 667 115 also discloses an intracorporeal probe that is designed in the form of a capsule that can be swallowed by the patient to be examined in order to be able to examine the gastrointestinal tract visually. The optical signals received from the probe are transmitted telemetrically via a transmitter present in the capsule to extracorporeal space and visualized there. This known autonomous video probe certainly enables visual inspection of the gastrointestinal tract, and permits the images to be transmitted to the outside telemetrically, but undertaking a diagnosis with the aid of the transmitted images is exceptionally difficult. The reason for this resides in the fact that, although the position of the probe inside the patient can be determined in the meantime relatively well, the regions picked up by the image sensor installed in the probe are of a rather random nature. It is not possible for specific regions inside the gastrointestinal tract to be specifically picked up. The image information obtained by the probe is consequently more of a random product and cannot be determined by the examining doctor.

Against this background, the invention is therefore based on the object of developing the intracorporeal probe mentioned at the beginning so as to enable a controlled, flexible and targeted visualization.

SUMMARY OF THE INVENTION

According to the invention, this object is achieved with regard to the intracorporeal probe mentioned at the beginning by virtue of the fact that the image pickup unit is held in a fashion capable of moving inside the housing in order to be able to vary the pickup region by means of such a movement.

That is to say, in other words, the alignment of the image pickup unit can be varied such that the straight ahead front view of previous probe solutions can be varied via an appropriate movement of the image pickup unit to provide a side view as well, without there being variation in the position of the probe itself. Overall, it is thereby possible for the field of view of the image pickup unit to be greatly enlarged by varying its position inside the probe.

The examining doctor obtains much more image information with the aid of the inventive probe while the probe is passing through the gastrointestinal tract.

In a preferred refinement, the image pickup unit has an image sensor and a pickup optics. The image pickup unit preferably has at least one illumination element for illuminating the pickup region.

The aforementioned measures have the advantage that a very compact image pickup unit is provided that owing to its movable mounting inside the housing of the probe moves the image sensor and pickup optics together. It is thereby possible to achieve a simpler control for the execution of a movement, since only one component need be moved.

The fact that the image pickup unit also has an illumination element, which means at the same time that the illumination element cooperates in the movement of the image sensor and the pickup optics, enables optimum illumination of the corresponding pickup region. The illumination element always illuminates the selected pickup region without requiring a dedicated control.

In a further preferred refinement, the housing is of elongated shape, and the image pickup unit is held in a fashion capable of swiveling about an axis that runs perpendicular to the longitudinal axis of the probe. It is preferred to provide a first motor that is coupled to the image pickup unit in order to move the latter. The motor is preferably a wobble motor, in particular a Q-PEM motor.

The aforesaid measures have proved to be particularly advantageous in practice. In particular, a very large pickup region is permitted by the ability of the image pickup unit to swivel about an axis that runs perpendicular to the longitudinal axis of the probe. The pickup region itself, that is to say the position of the image pickup unit, can be set via the first motor, preferably via control signals output by the examining doctor. Of course, it is also conceivable to control the motor in accordance with a permanently prescribed program without external influence.

The use of a wobble motor has proved to be advantageous as regards the aspects of energy and accuracy in particular. A wobble motor requires little energy and can be moved in very precise small incremental steps.

In a further preferred refinement, a coupling element is provided between the motor and image pickup unit and is designed to convert a rotary movement of the motor into a transverse movement. The coupling element is preferably fitted on the image pickup unit in a fashion remote from the swiveling axis, and the coupling element preferably comprises a flexible shaft.

These measures permit a very efficient swiveling of the image pickup unit about the axis perpendicular to the longitudinal axis. The flexible shaft in this case undertakes the swiveling of the image pickup unit when the motor rotates.

It goes without saying that the previously described approach to a solution for swiveling the image pickup unit about the transverse axis (with reference to the longitudinal axis of the probe) is a purely exemplary one. The person skilled in the art will recognize that other possibilities exist for appropriately coupling the image pickup unit to a motor in order to achieve a swiveling movement about the transverse axis. Thus, for example, the coupling of a motor to the image pickup unit could be performed via the transverse axis, that is to say the transverse axis or a corresponding transversely running shaft transmits the rotary movement of the motor to the image pickup unit.

In a further preferred embodiment, the image pickup unit is held in a fashion capable of rotating about the longitudinal axis of the probe.

This measure has the advantage that the pickup region can be greatly enlarged once more. By swiveling the image pickup unit about the transverse axis, and by rotation about the longitudinal axis it is possible to bring the image pickup unit into many more positions such that the pickup region can pick up at least a hemispherical region around the probe.

A second motor is preferably provided in order to rotate the image pickup unit about the probe longitudinal axis. With particular preference, the image pickup unit and the first motor are interconnected with the aid of the coupling element in order to be able to rotate jointly about the probe longitudinal axis.

In a further embodiment, a mounting frame that carries the image pickup unit and the first motor is provided in the housing, and is preferably coupled to the second motor for rotation about the probe longitudinal axis.

This is a conceivable solution for holding the image pickup unit and the two motors inside the probe. However, it will be clear to the person skilled in the art that there are further possible ways of holding the image pickup unit, the first motor and the second motor appropriately in the housing of the probe so as to ensure fluidity of swiveling about the transverse axis, and of rotating about the longitudinal axis.

In a further preferred embodiment, the image sensor is a CMOS image sensor, for example an HDRC (high dynamic range camera) type CMOS image sensor, preferably with a resolution of 768×496 pixels. The CMOS image sensor is preferably operated at an imaging rate of at least two, in particular ten, more preferably at least twenty images per second.

The aforesaid image sensor has proved in practice to be particularly advantageous, particularly with regard to its resolution and its photosensitivity. Such a type HDRC CMOS image sensor is described, for example, in German patent DE 42 09 536.

In a further preferred refinement, the probe has a transmitting unit for transmitting the acquired images from intracorporeal space to extracorporeal space, an energy receiving and supply unit that preferably receives energy inductively from extracorporeal space and supplies units inside the probe with energy, and a locating unit for locating the intracorporeal position of the probe from the extracorporeal.

The energy receiving and supply unit can be used to transfer into the probe energy from extracorporeal space that then serves to supply the respective elements, in particular the image pickup unit and the motors. The locating unit can be used for accurate determination of the position of the probe inside the gastrointestinal tract of the patient, the alignment or position of the longitudinal axis of the probe relating to this purpose, as well. These data enable the examining doctor on the one hand to be able to classify and evaluate the received images more effectively and, on the other hand, to have the motors controlled in a targeted fashion and thus to vary the pickup region.

It is thereby possible to pick up specific pickup regions deliberately such that the pictures of the gastrointestinal tract that are supplied are no longer random products. Consequently, the results of diagnosis can be much improved overall.

It may be remarked at this juncture that the aforesaid units, specifically transmitting unit, energy receiving and supply unit and locating unit can also be used separately of one another.

In a further preferred embodiment, the illumination element is a light-emitting diode. It is preferred to provide a number of light-emitting diodes that are arranged around the optics for uniform illumination of the pickup region.

On the one hand, light-emitting diodes are very compact components, while on the other hand they manage with relatively little energy in conjunction with a high light yield, something which renders them advantageous for use in an intracorporeal probe.

In a further preferred embodiment, an electroacoustic transducer is provided that generates an acoustic signal in the audible or in the ultrasonic range.

It is further preferred that in addition to the image sensor the image pickup unit has further electronic elements for processing the signals supplied by the image sensor.

This measure has the advantage that the image signals can be compressed, for example, even in the probe in order thereby to be able to lower the requisite data transmission rate or, vice versa, to be able to transmit more image data to extracorporeal space per time unit.

In a further preferred embodiment, the image pickup unit is arranged at a longitudinal end of the housing, and this end region of the housing is of dome-shaped and transparent design.

The arrangement of the image pickup unit at a longitudinal end has proved to be particularly advantageous with regard to the possible pickup region. However, it is to be remarked that the image pickup unit could also be arranged at other positions inside the probe. Moreover, it is conceivable that at least one further image pickup unit is provided in a movable fashion, for example in such a way that their pickup regions complement one another. For example, the image pickup units could be arranged such that—in the unswiveled state—their optical axes are perpendicular to one another.

This preferred refinement enables a further enlargement of the pickup region, and thus an improvement in the results of diagnosis, since more image information, for example from the gastrointestinal tract, is available to the examining doctor.

Further advantages and features emerge from the following description and the attached drawing. It goes without saying that the aforementioned features, and those still to be explained below, can be used not only in the respectively specified combination, but also in other combinations or on their own without departing from the scope of the present invention.

BRIEF DESCRIPTION OF THE DRAWINGS

Exemplary embodiments of the invention are illustrated in the drawing and will be described in more detail hereinafter with reference thereto, wherein.

DESCRIPTION OF PREFERRED EMBODIMENTS

Figure 1:
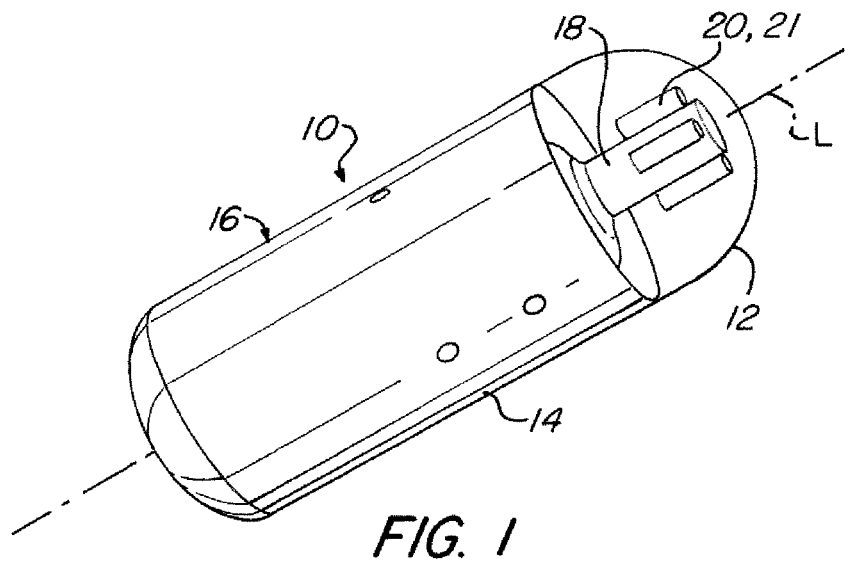
FIG. 1 shows a perspective view of an intracorporeal probe according to the invention.

An intracorporeal probe is shown in a perspective illustration in FIG. 1 and marked with the reference numeral 10. This probe 10 is used, for example, to examine hollow organs or body cavities in the human or animal body. In particular, the probe is used to examine the gastrointestinal tract of a patient. The probe 10 is swallowed for this purpose by the patient to be examined and thereafter travels through the gastrointestinal tract, finally being excreted again.

The probe 10 is of elongated shape, the longitudinal axis being indicated by dashes in FIG. 1, and being denoted by the letter L. The dimensions of the probe are selected such that the probe can be easily swallowed, and so they correspond approximately to the dimensions of conventional drug capsules.

The probe 10 has a dome-shaped longitudinal end 12 that is fabricated from an optically transparent material. By contrast therewith, the remaining part of the probe, which is denoted by the reference numeral 14, is fabricated from a nontransparent material. The longitudinal end 12 and the longitudinal section 14 adjoining it together form a liquid-tight and acid-resistant housing 16.

Visible in the region of the longitudinal end 12 behind the transparent dome is an optics 18 whose optical axis coincides in FIG. 1 with the longitudinal axis L. The optics 18 serves the purpose of focusing light from outside the probe onto an image sensor.

Provided in a fashion uniformly spaced around the optics 18 are illumination elements 20, the illumination elements 20 preferably being designed as LEDs 21. The LEDs 21 serve the purpose of illuminating a specific region outside the probe. The alignment of the LEDs 21 thus corresponds in essence to the alignment of the optics 18.

Figure 2:
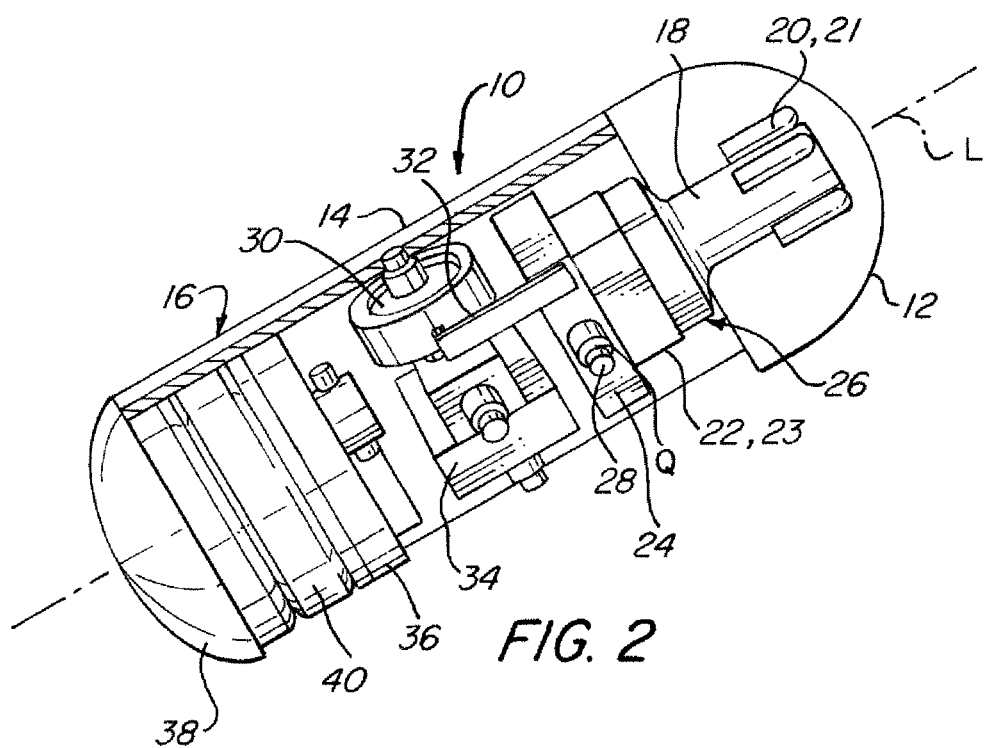
FIG. 2 shows a perspective illustration of the probe from FIG. 1 with partially opened housing.

The components provided inside the housing 16 are well in evidence in the illustration of FIG. 2. Following the optics 18 is an image sensor 22 that is preferably designed as a CMOS sensor 23. The image sensor 22 is seated, in turn, on a camera chip 24 that contains the logic circuitry required for evaluating the image signals supplied by the CMOS sensor.

The optics 18, the image sensor 22 and the camera chip 24 together form an image pickup unit 26. The aforesaid elements 18, 22 and 24 are consequently permanently interconnected and therefore can be handled as a unit. The camera chip 24 is connected inside the housing to two points thereof, one connecting point being visible in FIG. 2 and denoted by the reference numeral 28. The other connecting point (not visible) lies on an axis that goes through the connecting point 28 and cuts the longitudinal axis L. The connecting points 28 are designed such that a rotation of the camera chip 24 about a transverse axis Q (that is perpendicular to the longitudinal axis L and goes through the two connecting points 28) can be performed.

The entire image pickup unit 26, that is to say also the image sensor 22 and the optics 18, can be pivoted or swiveled about the transverse axis Q with the aid of this swiveling suspension of the camera chip 24. The consequence of such a swiveling movement is a variation of the optical axis by comparison with the longitudinal axis L, and thus a variation in the pickup region sensed by the image pickup unit 26.

Overall, the image pickup unit 26 is designed to sense a specific pickup region outside the probe, and supply the optical images of the pickup region to the examining doctor.

Following the image pickup unit 26 inside the probe 10, as seen in the longitudinal direction, is a positioning motor 30 that is connected to the camera chip 24 via a coupling element 32. The motor 30 is a rotary motor, for example in the form of a Q-PEM motor, a time motor or a piezomotor. The motor 30 and the coupling element 32 together have the task of swiveling the camera chip 24, and thereby the image pickup unit 26 about the transverse axis Q. In the present exemplary embodiment, the rotary movement of the motor 30 is transformed via the coupling element 32 into a transverse movement. The coupling element 32 can be designed, for example, as a flexible shaft that is displaced in the longitudinal direction via a cam on the motor 30.

Of course, the person skilled in the art is also familiar with other solutions that enable a swiveling movement of the image pickup unit 26. For example, instead of the rotary motor 30 it would be possible to use a linear motor for swiveling the image pickup unit 26.

Provided in the same longitudinal section as the motor 30 inside the housing 16 of the probe 10 is a locating chip 34 that can supply exact position information. A locating chip is described in detail as a position-detecting element for example in the application WO 03/024328 of the applicant, and so reference is made for the purpose of simplification to this printed publication and the corresponding disclosure content is incorporated by reference. The position-detecting means of the probe 10 can be designed, for example, as a coil system whose position can be detected via an external magnetic field detector.

Other solutions directed to locating, that is to say determining the position of the probe, for example inside the gastrointestinal tract, are, of course, also conceivable.

Following the locating chip 34 in the longitudinal direction is an energy and data transmission chip 36 that is responsible, on the one hand, for transmitting information from intracorporeal to extracorporeal space and, on the other hand, for receiving data, for example control signals, from extracorporeal space. Corresponding solutions for the transmission of such data are likewise described in the previously mentioned printed publication WO 03/024328. In addition, the chip is capable of receiving energy from extracorporeal space.

Finally, the probe 10 includes at least one battery 40 at the longitudinal end 38 opposite the longitudinal end 12. This battery 40 is designed such that it can supply sufficient energy to the aforementioned electronic components inside the probe 10.

The probe 10 usually contains additional coils that are not shown in the figures. These coils can be used to position the probe in the gastrointestinal tract by applying an appropriate magnetic field extracorporeally. The examining doctor can therefore control the position of the probe from outside.

All in all, the intracorporeal probe shown in FIG. 2 provides the examining doctor with a tool with the aid of which he obtains pictures of the gastrointestinal tract that are much more precisely targeted than has been possible to date using rigid image pickup units and position control solely by magnetic fields. A field of view of virtually 180° can be covered by swiveling the image pickup unit 26. In order further to improve the image quality, the optics 18 can have an objective that is focusable and/or zoomable or can be switched to macrophotography. The focus can be set, for example, via a magnetic drive (not illustrated in FIG. 2, however). The aforesaid preferred embodiment is of particular importance whenever the distance of the optics 18 from the inside of the dome-shaped longitudinal end 12 changes as a result of the swiveling movement of the image pickup unit.

Of course, other image sensors, for example CCD sensors, are also conceivable in addition to the abovementioned CMOS sensor 23. However, an HDRC (High Dynamic Range Camera) image sensor based on CMOS technology has proved to be particularly advantageous in practice. Such a logarithmically operating sensor is described in detail in DE 42 09 536, and so reference may be made thereto.

Figure 3:
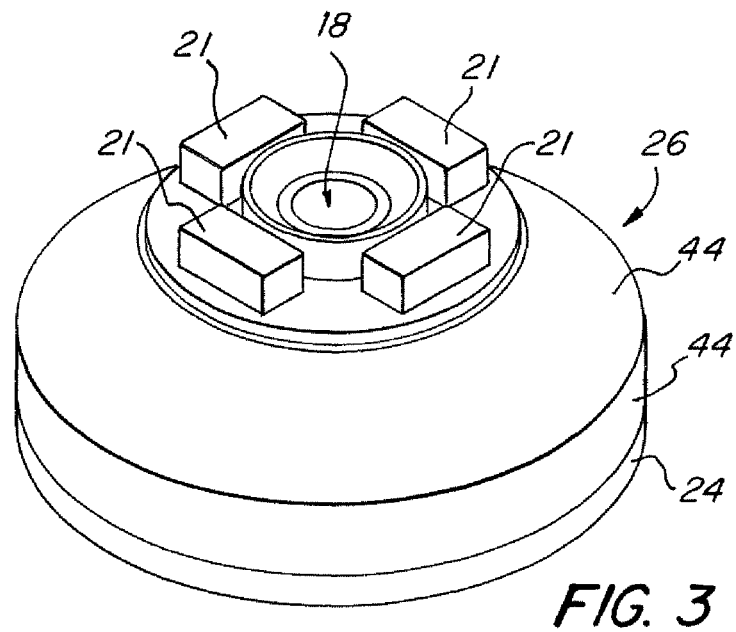
FIG. 3 shows a perspective schematic diagram of an image pickup unit.
Figure 4:
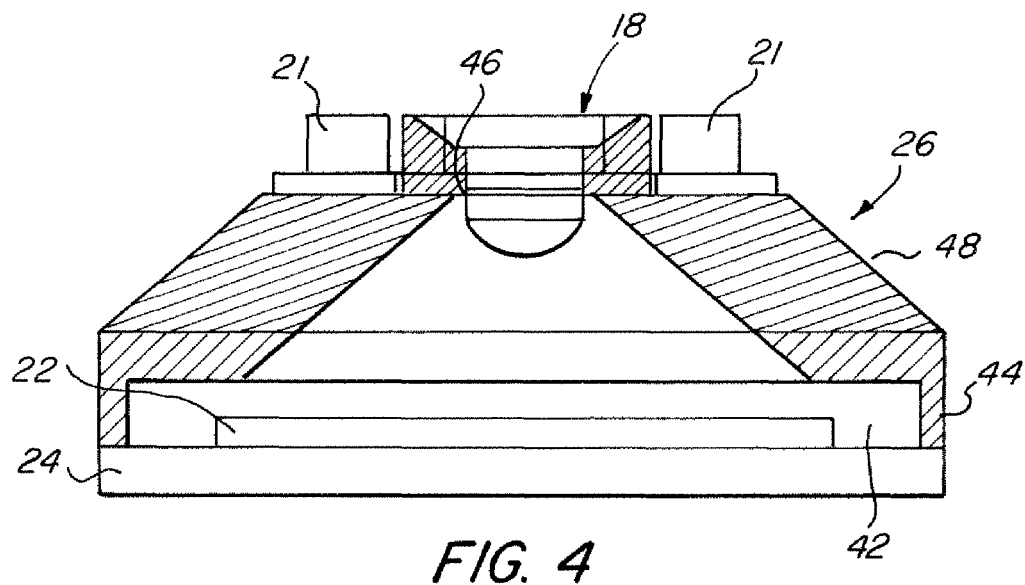
FIG. 4 shows a sectional schematic diagram of the image pickup unit from FIG. 3.

FIGS. 3 and 4 show an image pickup unit 26 that differs somewhat with regard to its shape from the image pickup unit illustrated in FIG. 2.

As already mentioned, the image pickup unit 26 comprises the camera chip 24, which has electronic components for processing image signals. On this camera chip 24, the image sensor 22 lies inside an interior 42 that is surrounded by a housing 44. The housing 44 is fabricated from an opaque material such that light can pass into the interior 42 only through an opening 46. Starting from the opening 46, the interior 42 expands conically toward the image sensor 22.

The upper longitudinal section 48 of the housing 44 also has this conical shape. The conical shape of the longitudinal section 48 enables a more effective possibility of swiveling inside the dome-shaped longitudinal end 12 of the probe 10.

The optics 18, which preferably includes a focusing objective, is provided in the opening 46.

The optics 18 is designed such that a region lying directly before the dome-shaped longitudinal end is focused onto the image sensor 22.

The LEDs 21 are arranged adjacent to the optics 18, use being made of a total of four LEDs in the present exemplary embodiment. Of course, a different number of LEDs is also possible.

The swivelability of the image pickup unit 26 will now be examined again with reference to FIGS. 5A-C.

Figure 5A:
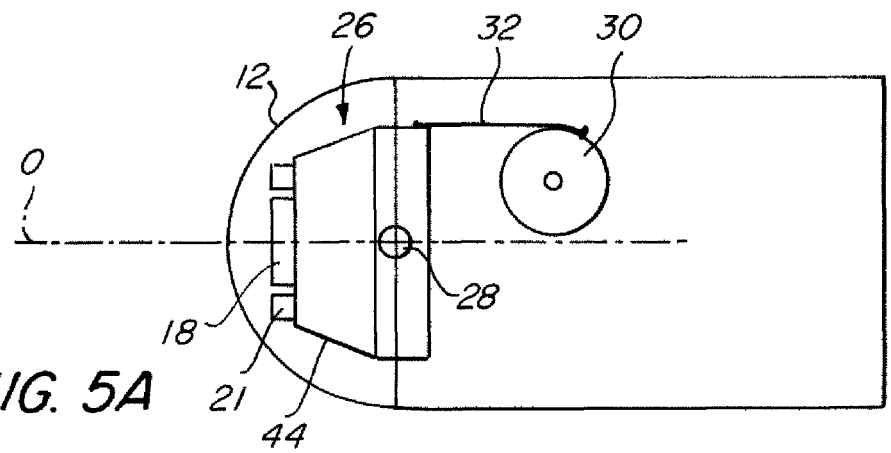
FIGS. 5A-C show a schematic diagram of the image pickup unit inside the probe for the purpose of explaining the inventive mobility of the image pickup unit.

The image pickup unit 26 is shown in FIG. 5A in its fundamental position, in which the optical axis, denoted by O, coincides with the longitudinal axis L of the probe 10.

Figure 5B:
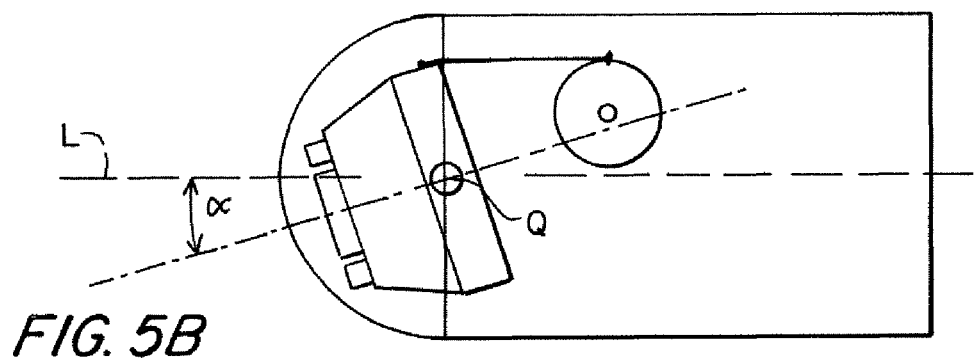
Figure 5C:
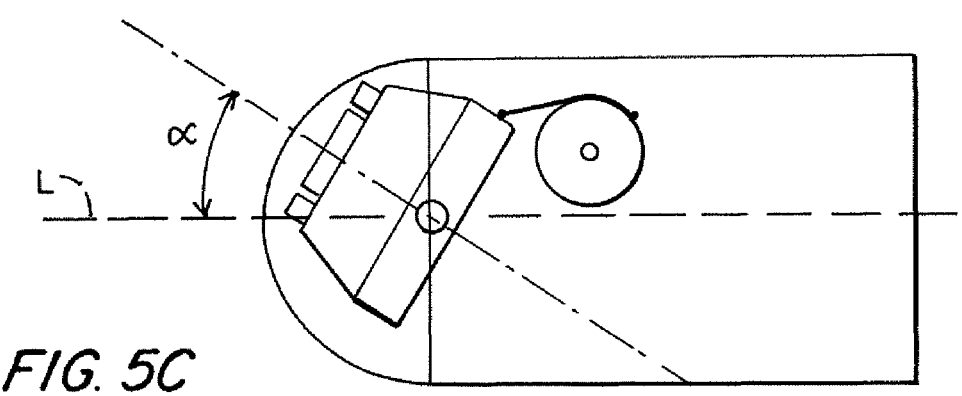

The motor 30 must be activated if the image pickup unit 26 is to be swiveled about the transverse axis Q. A stepwise rotation of the motor 30 leads to a displacement of the coupling element 32 and, owing to the fact that it is fitted offset from the transverse axis Q, to a swiveling of the image pickup unit 26. In FIG. 5B, the image pickup unit 26 is swiveled counterclockwise by an angle α, while in FIG. 5C the swiveling has been performed in a clockwise fashion by the angle α. The two maximum values of the angles α are preferably designed such that a pickup region of virtually 180° can be detected by the image pickup unit.

As already mentioned, the person skilled in the art is familiar with different solutions of achieving the above-described swivelability of the image pickup unit 26 about the transverse axis Q. The invention is not intended to be limited to the illustrated solution with a rotary motor and a shaft as coupling element.

In order to achieve swiveling of the image pickup unit 26, it is preferred to control the motor 30 via control signals that are output by the examining doctor. Control signals can be received by the data transmission chip 36 and be processed to form control signals for the motor 30. Of course, it is also conceivable to run the swiveling of the image pickup unit 26 via a permanently prescribed control program stored in the electronics of the probe 10.

The images supplied by the image pickup unit 26, preferably ten images per second, are processed by the logic circuitry on the camera chip 24, in particular compressed in order then to be transferred to extracorporeal space for the purpose of visualization for the examining doctor. The processing of the image signals on the camera chip 24 can be taken over, for example, by an ASIC designed therefor.

The image information supplied to the examining doctor is linked to positional information that is supplied by the locating chip 34. The examining doctor therefore has the possibility of assigning the image information obtained to a specific region, for example inside the gastrointestinal tract.

The energy required to supply the electronic components inside the probe 10 is supplied by the battery 40. However, it is also conceivable for the energy, or at least a portion of the required energy, to be fed from outside. To this end, the energy and data transmission chip 36 can have three orthogonal coils and a stack of thick film substrates that fix and connect the receiver's electronic components. The three coils can be pushed into one another in order to form a compact cylinder that surrounds the electronic components. Because of the orthogonality of the coils, at least always one coil is capable of extracting energy from the external magnetic field independently of the position and alignment of the probe.

Figure 6:
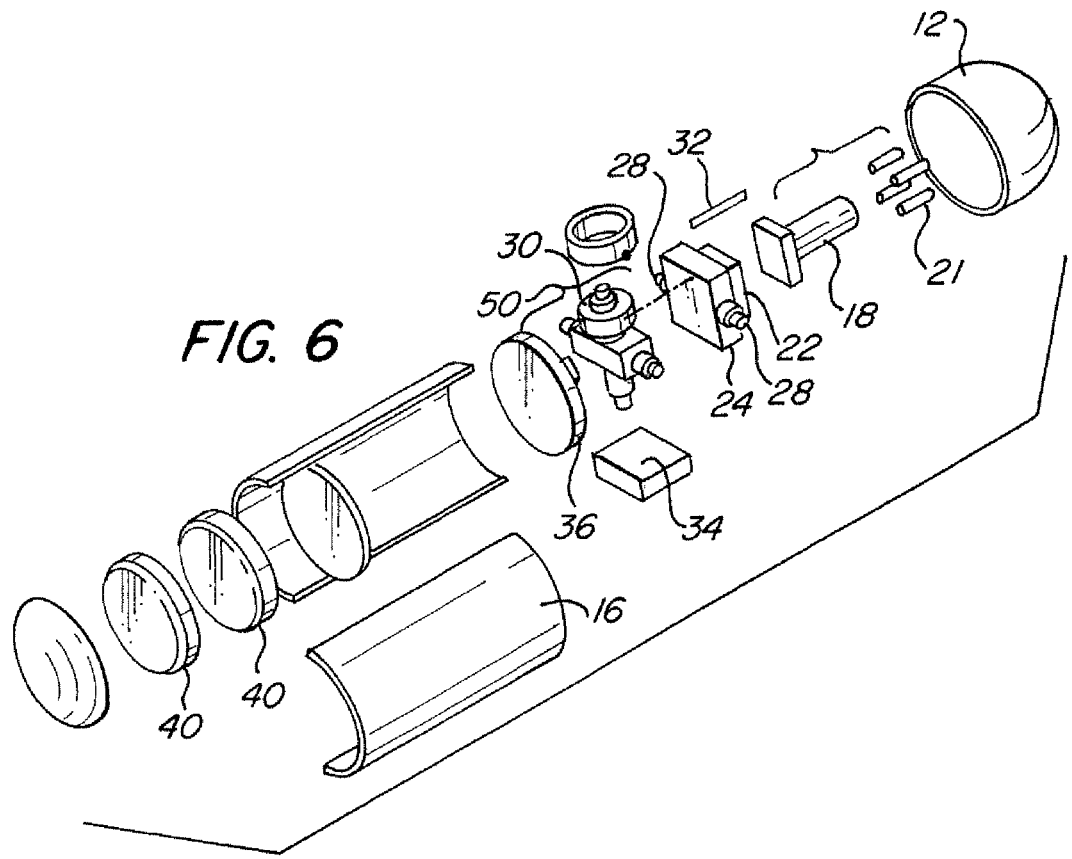
FIG. 6 shows an exploded schematic diagram of the inventive probe.
Figure 7:
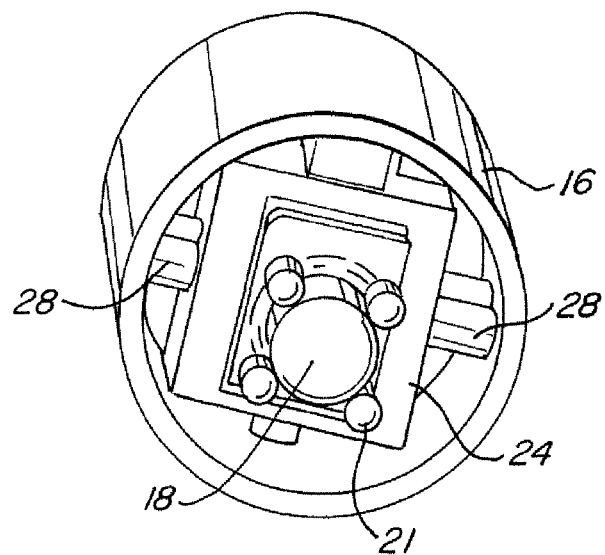
FIG. 7 shows a perspective schematic diagram of a longitudinal section of the probe that contains the image pickup unit.

The probe of FIG. 2 is shown once again in another illustration in FIGS. 6 and 7. Identical components are marked with identical reference numerals for the sake of simplicity. It is clearly to be seen from the two FIGS. 6 and 7 that the camera chip 24, and thus the image pickup unit 26 overall, is rotatably fitted on the housing 16 via two connecting points 28. Also to be seen are the cable connections 50 that run from the data transmission chip 36 to the camera chip 24 and the motor 30. Also well in evidence is the dome-shaped longitudinal end 12 that is fabricated from a transparent material, preferably glass.

Figure 8:
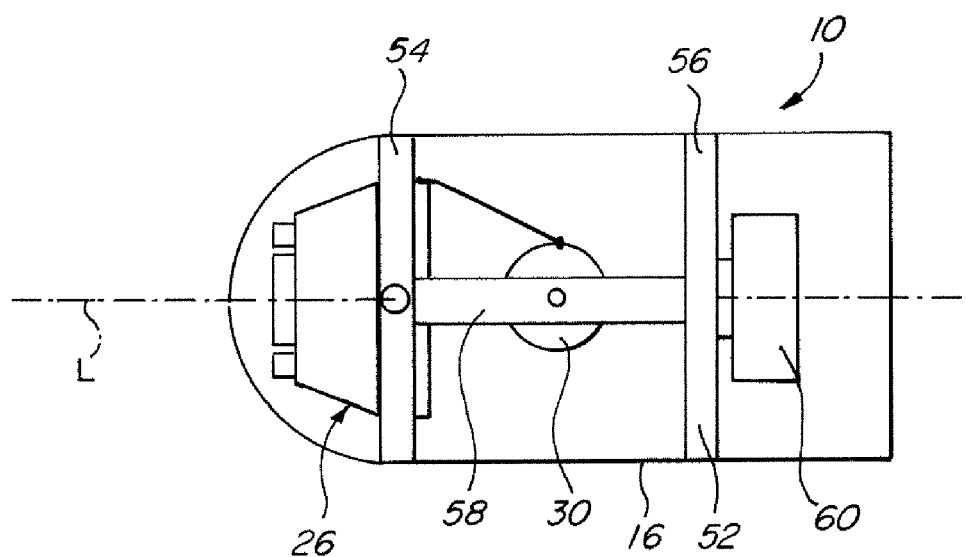
FIG. 8 shows a schematic diagram of a further embodiment of the intracorporeal probe for the purpose of achieving the ability to rotate about the longitudinal axis.

With reference to FIG. 8, a further embodiment of the inventive intracorporeal probe 10 will now be described that differs from the previous probe only in that the image pickup unit 26 is also held in a fashion capable of rotating about the longitudinal axis L.

To this end, the motor 30 and image pickup unit 26 are held by a frame 52 that can rotate inside the housing 16 about the longitudinal axis L. For example, the frame 52 could comprise two rings 54, 56 that are supported on the inside of the housing. The two rings 54, 56 are interconnected via one or more elements 58 running in the longitudinal direction. The motor 30 is fastened on such a longitudinally running element 58 (longitudinal carrier) in the example shown in FIG. 8.

The rotation of the frame 52, and thus of the image pickup unit 26, about the longitudinal axis L is performed via a second motor 60, which is permanently connected to the housing 16 and, for example, cooperates with the ring 56 in order to rotate the frame 52. Of course, other technical solutions can also be presented for the purpose, on the one hand, of holding the image pickup unit 26 and the motor 30 in a fashion capable of rotating about the longitudinal axis L, and, on the other hand, of undertaking the drive.

The rotatability of the image pickup unit 26 about the longitudinal axis L expands the possible pickup region in such a way that virtually the entire region about the dome-shaped longitudinal end 12 can be detected.

As also in the case of the motor 30, the motor 60 is preferably controlled via control signals output from extracorporeal space. However, the motor 60 could also be controlled via a permanently prescribed program.

A single image pickup unit 26 is provided in the probe 10 in the previously described exemplary embodiments. However, it is also conceivable to provide the image pickup unit 26 additionally at the opposite longitudinal end such that the pickup region is much enlarged.

Finally, it is also conceivable to provide two swiveling image pickup units 26 at a longitudinal end of the probe 10, or to provide an image pickup unit whose optical axis runs perpendicular to the longitudinal axis L and permits visual detection of the region at the lateral housing 16.

The inventive intracorporeal probe could also be combined with a probe such as is disclosed in the printed publication WO 03/024328 already previously mentioned.

It may be stated in summary that a substantial improvement is possible, in particular with regard to the targeting accuracy of the imaging, with the aid of the inventive swiveling arrangement of the image pickup unit 26

What is claimed is:

1. An intracorporeal probe, for example preferably for examining hollow organs or natural or artificially created body cavities in the human or animal body, comprising:
   a capsule-shaped housing that can be introduced into the body without external connecting elements, the housing being of elongated shape having a longitudinal axis;
   an image pickup unit inside the housing that is designed for optically recording a pickup region outside the probe and is held in a fashion capable of swiveling about a swiveling axis that runs perpendicular to the longitudinal axis of the probe and capable of rotating about the longitudinal axis inside the housing in order to vary the pickup region by means of swiveling about the swiveling axis and rotating about the longitudinal axis; and
   a wobble motor coupled to the image pickup unit that swivels the image pickup unit about the swiveling axis,
   a mounting frame provided in the housing and carrying the image pickup unit and the wobble motor, wherein the mounting frame is coupled to a second motor for rotation about the longitudinal axis.

2. The probe as claimed in claim 1, wherein the image pickup unit has an image sensor and a pickup optics.

3. The probe as claimed in claim 2, wherein the image sensor is a CMOS image sensor.

4. The probe as claimed in claim 3, wherein the CMOS image sensor is operated at an imaging rate of at least two images per second.

5. The probe as claimed in claim 4, wherein the CMOS image sensor is operated at an imaging rate of at least twenty images per second.

6. The probe as claimed in claim 3, wherein the image sensor is an HDRC (high dynamic range camera) type CMOS image sensor.

7. The probe as claimed in claim 6, wherein the image sensor has a resolution of 768×496 pixels.

8. The probe as claimed in claim 1, wherein the image pickup unit has at least one illumination element for illuminating the pickup region.

9. The probe as claimed in claim 8, wherein the illumination element is a light-emitting diode.

10. The probe as claimed in claim 9, wherein a number of light-emitting diodes are provided that are arranged around the optics for uniform illumination of the pickup region.

11. The probe as claimed in claim 1, wherein an electroacoustic transducer is provided that generates an acoustic signal in the audible or in the ultrasonic range.

12. The probe as claimed in claim 1, wherein the capsule-shaped housing comprises a transparent dome at its longitudinal end and the image pickup unit is arranged at least partially within the transparent dome.

13. The probe as claimed in claim 12, wherein the image pickup unit has a conically-shaped exterior that allows it to move freely within the transparent dome.

14. The probe as claimed in claim 1, wherein at least one further image pickup unit is provided in a movable fashion.

15. The probe as claimed in claim 14, wherein the further image pickup unit is arranged such that their pickup regions complement one another.

16. The probe as claimed in claim 15, wherein the further image pickup unit is arranged at the opposite longitudinal end of the housing.

17. An intracorporeal probe for examining hollow organs or natural or artificially created body cavities in the human or animal body, comprising:
   a capsule-shaped housing that can be introduced into the body without external connecting elements, the housing having a longitudinal axis;
   an image pickup unit inside the housing that is designed for optically recording a pickup region outside the probe and is held in a fashion capable of moving inside the housing in order to vary the pickup region by means of such a movement;
   a first motor coupled to the image pickup unit that swivels the image pickup unit about a swiveling axis, the swiveling axis running perpendicular to the longitudinal axis; and
   a coupling element provided as a flexible shaft between the first motor and image pickup unit remote from the swiveling axis, the first motor displacing the flexible shaft as to swivel the image pickup unit; and
   a second motor provided in order to rotate the image pickup unit about the longitudinal axis of the housing,
   wherein the image pickup unit and first motor are interconnected with the aid of the coupling element in order to be able to rotate jointly about the longitudinal axis,
   wherein a mounting frame that carries the image pickup unit and first motor is provided in the housing, and
   wherein the mounting frame is coupled to the second motor for rotation about the probe longitudinal axis.

18. An intracorporeal probe for examining hollow organs or natural or artificially created body cavities in the human or animal body, comprising:
   a capsule-shaped housing that can be introduced into the body without external connecting elements, the housing having a longitudinal axis;
   an image pickup unit inside the housing that is designed for optically recording a pick up region outside the probe and is held in a fashion capable of moving inside the housing in order to vary the pickup region by means of such a movement;
   a first motor coupled to the image pickup unit by a flexible shaft which shaft swivels the image pickup unit about a swiveling axis being perpendicular to the longitudinal axis;
   a second motor provided in order to rotate the image pickup unit about the longitudinal axis of the housing;
   a mounting frame provided in the housing and carrying the image pickup unit and the first motor, wherein the mounting frame is coupled to the second motor for rotation about the longitudinal axis;
   a signal receiving unit that receives control signals from extracorporeal space; and
   a control program that controls the first and second motors according to the control signals.

19. The probe as claimed in claim 18, defined by
   a transmitting unit for transmitting the acquired images from intracorporeal space to extracorporeal space;
   an energy receiving and supply unit that preferably receives energy inductively from extracorporeal space and supplies units inside the probe with energy, and
   a locating unit for locating the intracorporeal position of the probe from the extracorporeal.

20. The probe as claimed in claim 18, wherein in addition to the image sensor the image pickup unit has further electronic elements for processing signals supplied by the image sensor.

21. The probe as claimed in claim 18, wherein the control program and signal receiving unit are located on the same chip.

\* \* \* \* \*